United States Patent [19] [11] 3,944,612
Bil [45] Mar. 16, 1976

[54] 4-FLUORO-3-NITRO ANILINES

[75] Inventor: Milos S. Bil, Forest Hills, N.Y.

[73] Assignee: Clairol Incorporated, New York, N.Y.

[22] Filed: Nov. 27, 1970

[21] Appl. No.: 93,465

Related U.S. Application Data

[62] Division of Ser. Nos. 683,758, Nov. 2, 1970, abandoned, and Ser. No. 719,682, April 8, 1968, Pat. No. 3,632,582.

[52] U.S. Cl. 260/573; 260/247.5 R; 260/293.72; 260/293.79; 260/326.5 L; 260/326.85; 260/465 E; 260/471 A; 260/471 C; 260/508; 260/518 A; 260/551 C; 260/556 AR; 260/556 B; 260/558 R; 260/558 A; 260/561 R; 260/561 B; 260/562 R; 260/567.6 M; 260/570.5 P; 260/576; 260/577; 260/578
[51] Int. Cl.² C09B 87/60; C09B 91/06
[58] Field of Search 260/573, 577

[56] References Cited
UNITED STATES PATENTS

| | | | |
|---|---|---|---|
| 2,202,902 | 6/1940 | Ellis et al. | 260/573 X |
| 3,377,352 | 4/1968 | Clark et al. | 260/286 |
| 3,629,330 | 12/1971 | Brody et al. | 260/577 X |

FOREIGN PATENTS OR APPLICATIONS

| 1,398,576 | 3/1965 | France | 260/141 |
|---|---|---|---|

OTHER PUBLICATIONS

Ainsworth et al., "Preparative Routes to T-Amine-Substituted Nitroanilines," J. Chem. Soc., 1966, No. 1, pp. 111–113.
Chemical Abstracts, Vol. 47, (1953), 1133h,i–1134a.
Chemical Abstracts, Vol. 58, (1963), 14171f.
Chemical Abstracts, Vol. 58, (1963), 9085e.
Chemical Abstracts, Vol. 52, (1958), 9149a.

*Primary Examiner*—Charles F. Warren
*Attorney, Agent, or Firm*—Irving Holtzman; George A. Mentis; David J. Mugford

[57] ABSTRACT

Compounds of formula:

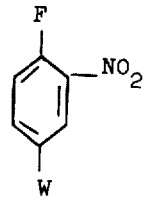

wherein W is

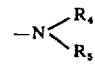

or

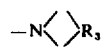

in which: (a) $R_4$ and $R_5$ are 5 identical or different and represent hydrogen, monovalent aliphatic, substituted or unsubstituted aryl, aralkyl and cycloalkyl, providing that not more than 1 of $R_4$ or $R_5$ is hydrogen, and (b) $R_3$ is a divalent aliphatic radical.

3 Claims, No Drawings

4-FLUORO-3-NITRO ANILINES

This application is a division of Application Ser. No. 683,758, filed Nov. 2, 1967, now abandoned, and of Application Ser. No. 719,682 filed Apr. 8, 1968, now U.S. Pat. No. 3,632,582.

This invention relates to a process for preparing nitro-p-phenylenediamines and to certain novel compounds relating to the same. More particularly, this invention concerns certain 4-fluoro-3-nitro-anilines (i.e., N-substituted and unsubstituted); their use in preparing nitro-p-phenylenediamines and certain novel compounds.

The nitro-p-phenylenediamines have been found to be useful as dyes, particularly in the dyeing of human hair. This is illustrated, inter alia, by reference to U.S. Pat. Nos. 2,750,327; 3,088,978; 3,168,442; 3,088,877; 3,119,867; 3,088,878 and 3,274,249 which describe a variety of nitro-p-phenylenediamines and their use in dyeing human hair.

A number of processes are known in the prior art for preparing compounds of this series. However, they all leave something to be desired. Thus, for example, it has been proposed to prepare the nitro-p-phenylenediamines by the nitration of certain p-phenylenediamines. This procedure required the previous blocking of the H atoms on the amino N by means of acetylation, formylation, oxalylation, tosylation or the preparation of the urethane before the nitration step. It further required a hydrolysis step subsequent to the nitration reaction. This process, obviously, is very complicated and time-consuming and gives low overall yield, and accordingly, is not very useful from a commercial point of view.

Another proposed method utilizes the partial reduction of the dinitrocompound, i.e.,

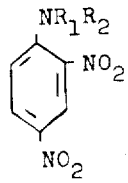

In this method, generally, two isomers are formed and, even when one isomer predominates, the separation is difficult and tedious. Moreover, (depending on the reducing agent and reaction conditions) the product of complete reduction is also often formed to some extent, which further complicates the separation of the desired compound.

The reducing agents used is this process have been quite varied and include sulfides or polysulfides of alkali metals, hydrosulfite, stannous chloride, metals in acid, hydrogen in the presence of catalysts (Pt, Pd, Ni). Recently, hydrazine in the presence of a catalyst (Ni, Pd, Pt) and the transfer hydrogenation (cyclohexene in the presence of Pd) have been employed. There is, however, no general rule as to which nitro group is reduced. With many alkaline reductions the o-diamino compound prevails in the reaction mixture; with many catalytic reductions in acid medium, the p-diamino isomer is predominant.

It has now been found unexpectedly that the nitro-p-phenylenediamines of interest may be prepared under relatively mild conditions, in very high yield and in a high state of purity by reacting a 4-fluoro-3-nitroaniline (N-substituted or unsubstituted) with the desired amine or ammonia.

It is accordingly an object of the present invention to provide a process for preparing nitro-p-phenylenediamines under mild conditions, in high yield and high degree of purity, employing a 4-fluoro-3-nitro-aniline (N-substituted or unsubstituted).

It is a further object of this invention to provide novel 4-fluoro-3-nitroanilines which are useful as starting materials in the process of the above object and to provide a novel process for preparing said 4-fluoro-3-nitroanilines.

It is still a further object of this invention to provide certain novel nitro-p-phenylenediamines.

Other and more detailed objects will be apparent from the following description and claims.

The principal process of the present invention can be described by the following equation:

(I) 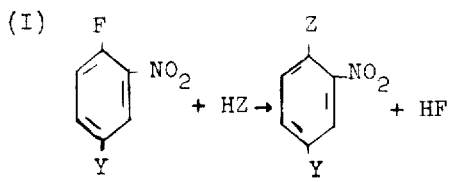

wherein HZ is an amine or ammonia and wherein:

a. Y and Z are

or

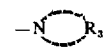

in which $R_1$ and $R_2$ might be identical or different and represent H, monovalent aliphatic, aryl, aralkyl, cycloalkyl radicals and $R_3$ is a divalent aliphatic radical.

All the compounds made by the process described in equation I above are useful as dyes, particularly for dyeing human hair. In addition, many are suitable as dye intermediates, pharmaceuticals, preparative organics or dyes for special purposes.

When $R_1$ and/or $R_2$ in equation I above is a monovalent aliphatic radical, it may take a variety of forms. Thus, it may be a straight-chain or branched-chain alkyl group; a monohydroxy or polyhydroxy (e.g., dihydroxy, trihydroxy) alkyl group; or a group like —CO—alkyl, —CO—hydroxyalkyl, —COO—alkyl, -CON(alkyl)$_2$, —CONH$_2$, —CSNH$_2$, —CN, —CH$_2$CONH$_2$, —SO$_2$—alkyl, —SO$_2$—aryl or a substituted alkyl group of the form —alkylene-M in which M may be —COOH, —CONH$_2$, —CO—alkyl, —CO—hydroxyalkyl, —SO$_3$H, —SO$_2$NH$_2$, —SO$_2$NH—alkyl, —SO$_2$—NH—hydroxyalkyl, —SO$_2$N(alkyl)$_2$,

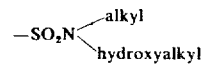

—SO$_2$N—(hydroxyalkyl)$_2$, —SO$_2$—alkyl, —NH$_2$, —NH—alkyl, —N(alkyl)$_2$, —N(alkyl)$_3$ + Cl$^-$, —(NH-alkylene)$_n$NH$_2$ or —(NH-alkylene)$_n$ OH, in which $n$ is a number from 1 to 3, —NHCO—alkyl, —NHCO—hydroxyalkyl, —NHCO—aryl, —NHCONH₂, —NHCSNH₂, NHCOO—alkyl, —NHSO₂—alkyl, —NHSO₂—aryl, —O—alkyl, —O—alkylene—OH, —CN. In the preferred form of this invention, the alkyl or the alkylene moieties above per se or in the hydroxyalkyl radical contain from 1 to 6 and particularly from 1 to 3 carbon atoms.

Typical among the monovalent aliphatic radicals which represent $R_1$ or $R_2$ in equation I above there can be mentioned: methyl, ethyl, n-propyl, isopropyl, n-butyl sec. butyl, tert. butyl, n-amyl, isoamyl, n-hexyl, 2-hydroxyethyl, 3-hydroxypropyl, 2-hydroxypropyl, tris(hydroxymethyl)methyl; 1,3-dihydroxy-2-methyl-2-propyl; 2,3-dihydroxypropyl; 1,3-dihydroxy-2-propyl; 2-diethylaminoethyl; aminopropylaminopropyl, methoxyethyl, ethoxyethyl, acetamidoethyl, propionamidoethyl, aminoethyl, aminopropyl, glycolamidopropyl, methylsulfonamidoethyl, propylsulfonamidopropyl, ureidopropyl, ureiodethyl, thioureidoethyl, carbethoxyaminoethyl, sulfamoylethyl, (2-hydroxyethylsulfamoyl)ethyl, dimethylsulfamoylethyl, cyanomethyl, acetyl, formyl, tosyl, cyanoethyl, di-alkyl-carbamoyl, carboxymethyl, etc.

When $R_1$ and/or $R_2$ in equation I above is aryl, it ordinarily will be a monocylic or a bicyclic aryl radical having up to 10 carbon atoms in the ring system. These usually will take the form of substituted and unsubstituted phenyl or naphthyl radicals. The arylsubstituted radicals can contain any of a variety of substituents or combinations thereof. By way of illustration, the following may be mentioned: alkyl, alkenyl, hydroxy, alkoxy, halogen, nitro, amino, alkylamino, dialkylamino, hydroxyalkylamino, carboxy, carbamoyl, carbalkoxy, cyano, mercapto, alkylthio, etc.

When $R_1$ and/ or $R_2$ in equation I above is an aralkyl radical, it will be similar in structure to that described above for the aryl radicals, excepting that the bonding to the amine nitrogen will be through the alkyl moiety of the aralkyl radical.

$R_3$ in equation I above is a divalent radical which together with the N atom forms a heterocyclic ring structure. $R_3$ may be a hydrocarbon radical or it may be an ether linked or N-linked hydrocarbon radical. Ordinarily, the ring system comprising $R_3$ and N will not contain more than 6 atoms (and usually will contain 5 or 6 atoms), and may be substituted or unsubstituted. By way of illustration it may be mentioned that the group

may be substituted or unsubstituted N-pyrrolidinyl, N-morpholinyl, N-piperazinyl, or N-piperidinyl radicals in which the substituents may be alkyl, halogen, alkoxy, etc.

When $R_1$ and/or $R_2$ above is cycloalkyl, it will ordinarily not exceed 6 carbon atoms and usually will contain 5 or 6 carbon atoms.

The principal process of the present invention involves the nucleophilic displacement of the fluorine atom by an amine or ammonia in the compound of the formula:

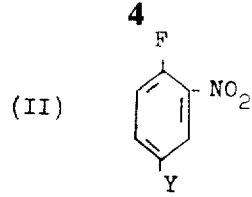

in which Y has the same value ascribed to it above in connection with equation I, under mild conditions and in good yields. This was indeed quite unexpected since the displacement of the other halogen atoms, such as chlorine, bromine or iodine, with amines is known to be very difficult. It is known that the presence of the Y group in the 1 position of the benzene ring (see formula II) deactivates a chlorine, bromine or iodine which would be present in the 4 position, so that displacement of these halogens by an amine is very difficult. Thus, very high temperature (e.g., 100° to 200°C) and high pressures (sealed tube or autoclave) must be used and even then the yields are very poor and are accompanied by resin formation and difficulties in the separation procedures. This deactivation effect is known in this art and is sometimes referred to as the +T effect. It was unexpected that the use of the corresponding fluorine compounds would so greatly facilitate the introduction of a second amino group into the 4 position.

The principal process of this invention involves condensing the amine or ammonia and the fluorine reactant under mild conditions. This will be effected at a temperature of no higher than about 100°C. and usually at the reflux temperature. Furthermore, the reaction will ordinarily not be carried out at a pressure that is above 100 P.S.I., and for the most part, only at atmospheric pressure. The process will proceed in any suitable solvent, usually water or aqueous alcohol being adequate. The use of dipolar aprotic solvents (DMT, DMSO, acetonitrile) is not necessary, although they may be included in some cases to speed up the rate of reaction.

The present method of preparation has several advantages over the prior art procedures:

a. only one isomer is formed by displacement of fluorine;

b. yields are very high and in most cases about quantitive;

c. only mild conditions for the reaction are necessary;

d. inexpensive solvents can be used as the reaction medium;

e. expensive catalysts (Pt, Pd), which are used in some prior art processes, are eliminated. This is important since in a large scale production, they constitute the major item in the cost of the product;

f. purity of the product is enhanced; and g. working up of the reaction mixture is simplified.

It is another object of the present invention to provide a process for preparing the intermediate fluorine product and the corresponding compounds that are useful in the principal process described in equation 1 above. These intermediates have the general formula II, shown above, and can be prepared by the nitration of the appropriate p-fluoroaniline (i.e., N-substituted or unsubstituted and may be described generally by the following:

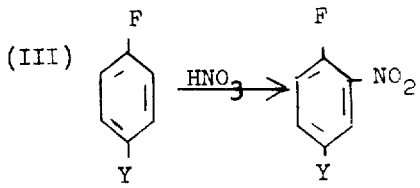

wherein Y has the same significance ascribed to it in connection with equation I above. In a preferred method for preparing the 4-fluoro-3-nitro-anilines involved in the present invention, the nitrating agent comprises a mixture of sulfuric and nitric acid, and the reaction is carried out at low temperatures (e.g., 3°–5°C.).

As an alternative procedure for synthesizing the substituted compounds of formula II above, 4-fluoro-3-nitroaniline is first prepared by nitrating p-fluoroaniline. The 4-fluoro-3-nitroaniline so made is then reacted with an appropriate alkylating agent, e.g., alkyl or hydroxyalkyl compounds, alkylene oxides, alkyl sulfates, alkyl iodides, alkyl tosylates, alkylene chlorohydrin, or other appropriate reagents which will replace H bonded to the amine nitrogen in the 1 position. In this fashion one or both of the H atoms of the amine N may be replaced by the substituent $R_1$ or $R_2$ described above.

The nitrofluoroanilines of formula:

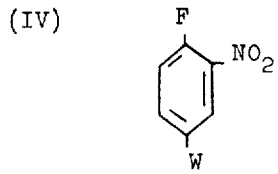

wherein
W is

or

and in which:
a. $R_4$ and $R_5$ are identical or different and have the same values ascribed above to $R_1$ and $R_2$ in equation I, excepting that only one of them may be hydrogen, and
b. $R_3$ is a divalent aliphatic radical also having the same values ascribed to $R_3$ in equation I;

form a novel group of compounds which are intermediates for the preparation of desired niro-p-phenylenediamine hair dyes described above.

It is another feature of the present invention to provide a novel group of nitro-p-phenylenediamines, which are likewise useful in dyeing human hair. This group is described by the formula:

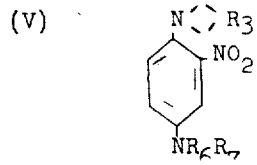

wherein:
a. $R_3$ is a divalent aliphatic radical having the same value as the $R_3$ defined above in connection with equation I; and
b. $R_6$ and $R_7$ are selected from the group consisting of hydrogen, alkyl and hydroxyalkyl; at least one of $R_6$ and $R_7$ being other than hydrogen. When $R_6$ and $R_7$ are alkyl or hydroxyalkyl, they will have the corresponding values ascribed to $R_1$ and $R_2$ above in connection with equation I.

The principal process of the present invention may be used to prepare a number of nitro-p-phenylenediamines which are known in the prior art to dye hair. The manner of using these materials in the dyeing of hair is adequately described in the U.S. patents cited above, and these are incorporated in this specification by way of reference. The compounds defined in formula V above may likewise be incorporated in similar hair dye compositions as those described in said U.S. patents. A typical composition in which the dyes of formula V above may be employed is prepared as follows:

A mixture defined below is diluted with 5.0 ml. water, and the whole heated at 60°C. for 1 hour:

| | |
|---|---|
| Dye | 0.25 g. |
| Ethanol | 0.35 g. |
| Ethanolamine | 4.0 g. |
| Sodium N-methyl-N-oleoyl-taurate (Igepon T-33) | 0.5 g. |
| Sodium carboxymethyl-cellulose | 3.0 g. |

This mixture was then further diluted with water to a volume of 100ml. and citric acid is added to give a pH of 9.9.

To dye hair, the dye compositons so obtained are poured on natural gray hair, permanent-waved hair or bleached hair and allowed to remain in contact therewith for 20 minutes at 30°C. The hair is then rinsed in clear water and dried in air. The following examples are further illustrative of the present invention. It should be understood, however, that the invention is not limited thereto.

EXAMPLE 1A

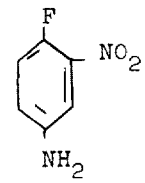

Preparation of 4-fluoro-3-nitroaniline

This process is a modication of the Holleman and Beckman procedure (Rec. trav. chim, Vol. 23 (1904) p. 237) by which there is obtained higher yields of recrystallized product. The procedure is as follows:

To a solution of 139 g. of p fluoroaniline in 1390 g. of $H_2SO_4$, 100%, a mixture of 81.3 g. $HNO_3$, 100%, in 810 g. $H_2SO_4$, 100%, is added at 3°–5°C. After 1 hour the mixture is poured on ice, neutralized with conc. ammonia, cooled. The solid obtained is filtered off, and recrystallized from boiling water. After cooling to 10°C, yellow-brown crystals are filtered off and dried.

Yield: 120 g. (=62% theory), m.p. 94° to 96°C (uncorr).

EXAMPLE 1B

Preparation of 4-fluoro-3-nitroaniline

To a solution of 139 g. of p-fluoroaniline in 834 g. of H₂SO₄, 100%, a mixture of 81.3 g. of HNO₃, 100% in 489 g. H₂SO₄, 100%, is slowly added at 8°–10°C. One hour after this addition, the mixture is poured on 800 g. of ice and the resulting solution made alkaline with 2300 ml. of conc. aqua ammonia. On cooling to approxiamtely 5°C., the orange crude product is filtered off, sharply sucked off, and stirred with 600 ml. of water and 120 ml. of conc. HCl at room temperature. The insoluble, dark-brown solid is filtered off, the filtrate made alkaline with 82 g. of solid sodium carbonate, and the solid filtered off and dried in vacuo at 60°–70°C or in the air.

Yield: 143 g., light orange crystals (= 73% theory), m.p. 95°–96°C.

EXAMPLE 2

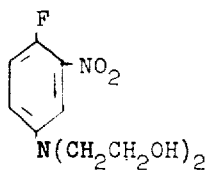

Preparation of 4-Fluoro-3-nitro-N,N-bis(Hydroxyethyl)-Aniline 78 g. of 4-fluoro-3-nitro-aniline is suspended in 250 ml. water and a stream of ethylene oxide is bubbled through at 70° to 80°C until the starting amine and the intermediate monohydroxyethyl derivative have disappeared. On cooling to 10°C light yellow crystals separate out, which are filtered off, washed slightly with water, and dried.

Yield: 112.5 g. (= 92.1% theory), m.p. 109°–110°C (uncorr.)

EXAMPLE 3

Preparation of N¹-(2-hydroxyethyl)-2-nitro-p-phenylenediamine

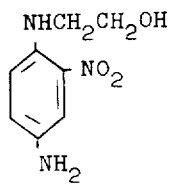

A mixture of:

| | |
|---|---|
| 4-fluoro-3-nitro-aniline | 15.6 g. |
| monoethanolamine | 13.5 g. |
| water | 100 ml. |
| sodium carbonate | 5.3 g. | is maintained at reflux until all starting amine disappears (ca. 4–5 hours). On cooling to room temperature a thick slurry is formed, which is filtered. A crystalline cake is obtained which is washed with water, and then dried.

Yield: 16.0 g. (= 81% theoretical) of bronze crystals, m.p. 121°–123°C (uncorr.), chromatographically pure (on paper).

EXAMPLE 4

Preparation of N¹-methyl-2-nitro-p-phenyleneadiamine

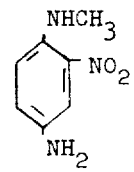

a. At normal Pressure: 7.8 g. of 4-fluoro-3-nitroaniline and 40 g. of 40% aq. solution of methylamine was held at 70° to 80°C with intermittent additions of portions of fresh methylamine solution until the reaction was completed. Evaporated water was replaced from time to time. On cooling, crystals of product separated, which were filtered off and dried.

Yield: 7.4 g. (= 89% theoretical) of dark bronze crystals, m.p. = 112.5°C. to 113.0°C, chromatographically pure.

(b) In autoclave: A mixture of:

| | |
|---|---|
| 4-fluoro-3-nitroaniline | 32.4 g. |
| methylamine, 40% | 120.0 g. | was held in a steel autoclave for 24 hours at 80° to 90°C and 12 to 28 P.S.I. After allowing to cool to room temperature, the slurry of crystals was filtered; the cake washed with warm water to remove a small amount of starting amine and methylamine, and finally dried.

Yield: 30.1 g. of dark bronze crystals (=87% theoretical), m.p. 109° to 110°C., chromatographically pure.

EXAMPLE 5

Preparation of 2-nitro-4-amino-(2'-diethylaminoethyl)-aniline

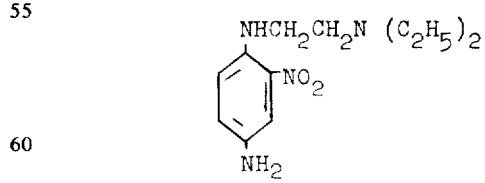

A mixture of:

| | | |
|---|---|---|
| 4-fluoro-3-nitroaniline | 3.12 | g. |
| N,N-diethylethylenediamine | 10.1 | g. |
| ethanol, 95% | 40 | ml. |
| Water | 10 | ml. |
| sodium acetate | 5 | g. | was maintained at reflux for several hours until most of the aromatic amine had reacted. The alcohol was distilled off, and sodium chloride added to precipitate the crystals of product, which were collected by filtration. This was then recrystallized from ethylacetate, and dried.

Yield: 1.2 g. of dark metallic crystals (= 24% theoretical), m.p. 127 to 128°C of ca. 95% purity by chromatogram.

EXAMPLE 6

Preparation of 2-nitro-4-amino-N,N-dimethylaniline

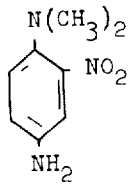

| 4-fluoro-3-nitroaniline | 3.90 g. |
| 25% aqueous solution of dimethylamine | 67.5 g. | was maintained at 55°C for about 3 hours. The dimethylamine was then removed on a steam bath, the residue extracted with ethyl acetate, and this extract evaporated on the steam bath. A dark oily product was obtained.

Yield: 3.4 g. (=75% theoretical), dark syrup, practically pure on chromatogram.

EXAMPLE 7

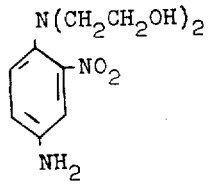

Preparation of 2-nitro-4-amino-N,N-bis(hydroxyethyl)-aniline

| 4-fluoro-3-nitroaniline | 3.90 g. |
| diethanolamine | 40. g. | were maintained at 80°C for 10 hrs. On cooling in an ice bath an oily layer separated, which was extracted with ethyl acetate. This extract was evaporated on a steam bath as far as possible. A brown thick oil resulted (10.4 g.), which was identified as a mixture of the product with diethanolamine.

EXAMPLE 8

Preparation of 2-nitro-4-amino-N-(tert-butyl)-aniline

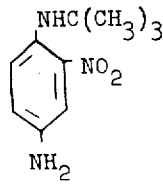

A mixture of:

| 4-fluoro-3-nitroaniline | 7.8 | g. |
| water | 150 | ml. |
| tert-butylamine | 19.35 | g. |
| sodium carbonate | 2.65 | g. | was maintained at reflux for 25 hours. On cooling to 5°C. a solid separated, which was washed with water to remove any butylamine, and microcrystals which were recovered were dried in desiccator over $H_2SO_4$.

Yield: 5.6 g (=53% of theoretical) of small bronze crystals, m.p. ca. 85°–87°C, ca. 95% pure by chromatography.

EXAMPLE 9

Preparation of $N^1$-[3'-(3''-aminopropylamino)propyl]-2-nitro-p-phenylenediamine

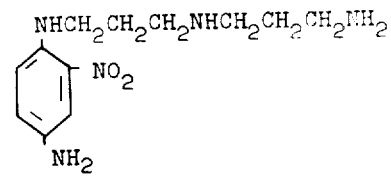

A mixture of 15.6 g.4-fluoro-3-nitroaniline, 13.7g. 3,3'-imino-bis-propylamine, 475 ml.water, and 5.3g. sodium carbonate was maintained at reflux for 5 hours. The reaction mixture was then allowed to cool to +5°C. A gummy crude product obtained was dissolved in acetone. A crystalline hydrochloride precipitated with conc. HCl, which was finally dried in a desiccator.

Yield: 18.7 g. of brown crystals (=70.2% of theoretical, calc. as dihydrochloride), m.p. 225°–226°C (decomposition above this temp.), ca. 97% purity by paper chromatography.

EXAMPLE 10

Preparation of $N^1$-cyclohexyl-2-nitro-p-phenylenediamine

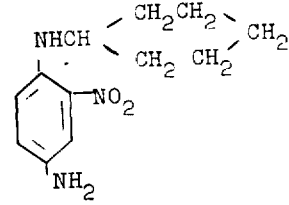

A mixture Of:

| 4-fluoro-3-nitroaniline | 6.24 | g. |
| cyclohexylamine | 7.92 | g. |
| water | 4 | ml. |
| isopropanol | 17 | ml. |
| sodium carbonate | 4.24 | g. |

EXAMPLE 11

Preparation of 1-(4-amino-2-nitrophenyl)pyrrolidine

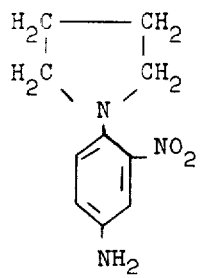

A mixture of:

| | |
|---|---|
| 4-fluoro-3-nitroaniline | 6.24 g. |
| pyrrolidine | 11.36 g. |
| ethanol-water (1:1) | 100 ml. | was mantained at reflux for 1½ hours. Ethanol was then evaporated, and a crude product isolated by cooling the mixture (8.0 g. = 97% of theoretical, m.p. 91.5°–95°C). On recrystallization from ethanol 5.0 g. of dark metallic crystals, m.p. 91.5°–95°C. was obtained.

EXAMPLE 12

Preparation of N-(4-amino-2-nitrophenyl)morpholine

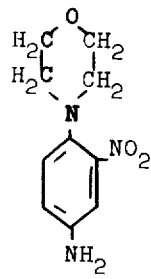

A mixture of:

| | |
|---|---|
| 4-fluoro-3-nitroaniline | 7.8 g. |
| morpholine | 21.8 g. |
| water | 250 ml. | was mantained at reflux for 8 hours. The mixture was allowed to cool, whereby large orange needles separated, which were filtered off and dried.

Yield: 10.7 g. light orange crystals (=96% theoretical), m.p. 133°–135°C, chromatographically pure. Saunders, J. Chem. Soc, 1955, 3286 (prepared by partial reduction of dinitrocompound) reports m.p. 133°–135°C.

EXAMPLE 13

Preparation of 1-(4-amino-2-nitrophenyl)piperidine

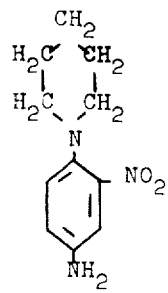

A mixture of:

| | |
|---|---|
| 4-fluoro-3-nitroaniline | 7.8 g. |
| piperidine | 21.0 g. |
| water | 250 ml. | was maintained at reflux for 8 hours. The mixture was allowed to cool, and fine crystals were filtered off, and dried.

Yield: 10.5 g. of dark violet crystals (=91% theoretical), m.p. 114°–116°C., Saunders, J. Chem. Soc., 1955, 3279 (prep. by partial reduction of dinitro compound) found m.p. 116°C (recryst. from ligroine).

EXAMPLE 14

Preparation of N$^1$,N$^4$,N$^4$-Tris(2-hydroxyethyl)-2-nitro-p-phenylenediamine

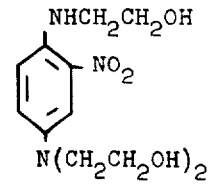

A mixture of:

| | |
|---|---|
| 4-fluoro-3-nitro-N,N-bis(2-hydroxyethyl)aniline | 24.4 g. |
| monoethanolamine | 13.5 g. |
| water | 100 ml. |
| sodium carbonate | 5.3 g. | was maintained at reflux for 1½ hour. At 75°C. the color of the mixture changed to a deep violet. After cooling to room temperature, the separated crystals were filtered off, ground, washed with 70 ml. of water, and dried.

Yield: 22.5 g. of dark metallic crystals (=79% theoretical), m.p. 100°–101°C, 99% purity by chromatographic analysis.

EXAMPLE 15

Preparation of
N¹-Methyl-N⁴,N⁴-bis(2-hydroxyethyl)-2-nitro-p-phenylenediamine

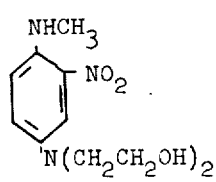

A mixture of:

| | |
|---|---|
| 4-fluoro-3-nitro-N,N-bis (2-hydroxyethyl)-aniline | 24.4 g. |
| methylamine, 40% aq. solution | 180 g. | was heated uniformly for 80 minutes to 73°C. At this point the reaction was completed. After allowing to cool spontaneously overnight and then to 5°C, a thick slurry of crystals was obtained which was ground in a mortar and filtered. The cake of fine crystals obtained was washed with water to neutrality and dried.

Yield: 21.7 g. of dark blue crystalline powder (=85% theor.), m.p. 98°C. chromatographically pure.

EXAMPLE 16

Preparation of
N¹-Isopropyl-N⁴,N⁴-bis(2-hydroxyethyl)-2-nitro-p-phenylenediamine

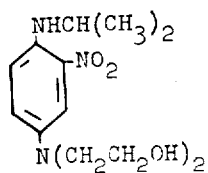

A mixture of:

| | |
|---|---|
| 4-fluoro-3-nitro-N,N-bis (2-hydroxyethyl)aniline | 24.4 g. |
| isopropylamine | 13.2 g. |
| water | 350 ml. |
| sodium carbonate | 5.3 g. | was maintained at reflux for 17 hours. On cooling, an oily layer separated, which was extracted with 250 ml. chloroform. This solution was evaporated until only a thick oil remained which was dissolved in 100 ml. of isopropanol and acidified with conc. hydrochloric acid. Sandy crystals of hydrochloride were obtained which were filtered off and dried in a desiccator over KOH and paraffin.

Yield: 8.9 g. of light yellow crystals (=28% theoretical, as monohydrochloride), m.p. 187°–188°C. chromatographically pure.

EXAMPLE 17

Preparation of
N¹-Tert.butyl-N⁴,N⁴-bis(2-hydroxyethyl)-2-nitro-p-phenylenediamine

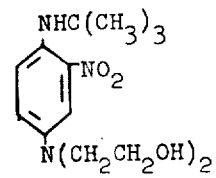

A mixture of:

| | |
|---|---|
| 4-fluoro-3-nitro-N,N-bis (2-hydroxyethyl)aniline | 19.52 g. |
| tert.-butylamine | 61.40 g. |
| water | 300 ml. |
| sodium carbonate | 4.24 g. | was maintained at reflux continuously for 30 hours. The reaction went to an 80–85% completion. On cooling, a dark heavy oil separated, which was washed with water, then extracted with chloroform, and this solution evaporated on the steam bath as far as possible. A sticky dark blue syrup resulted, which after standing in an open porcelain dish for about 1 week at room temperature, solidified to a crystalline body.

Yield: 21.0 g. (=88% theoretical), of ca. 85% purity (violet spot on chromatogram).

EXAMPLE 18

Preparation of
N¹-tris-hydroxymethylmethyl-N⁴,N⁴-bis(2-hydroxyethyl)-2-nitro-p-phenylenediamine

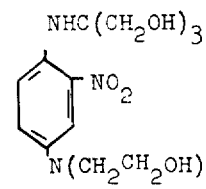

A mixture of:

| | |
|---|---|
| 4-fluoro-3-nitro-N,N-bis (2-hydroxyethyl)aniline | 15.9 g. |
| tris-hydroxymethylmethylamine | 29.8 g. |
| isobutanol | 33 ml. |
| water | 6 ml. |
| potassium carbonate | 6.0 g. | was maintained at reflux for 6 hours. After cooling, a gummy solid was filtered off and recrystallized from isopropanol.

Yield: 13.0 g. of dark blue powder (=52% theoretical), containing ca. 90% of pure product (violet spot on chromatogram).

EXAMPLE 19

Preparation of
1-[4-bis(2-hydroxyethyl)amino-2-nitrophenyl]pyrrolidine

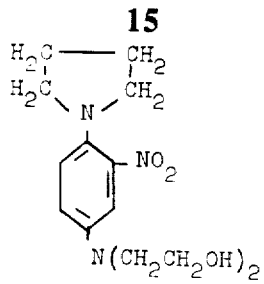

A mixture of:

| 4-fluoro-3-nitro-N,N-bis | | |
|---|---|---|
| (2-hydroxyethyl)aniline | 9.76 | g. |
| pyrrolidine | 8.52 | g. |
| ethanol-water (1:1) | 100 | ml. | was maintained at reflux for 2½ hours. Ethanol was then distilled off, some sodium cloride added, and after cooling in refrigerator, crystals separated, which were dried in desiccator.

Yield: 12.0 g. of purple needles (nearly quantitative yeild), m.p. 74°–76°C, chromatographically pure.

EXAMPLE 20

Preparation of N-[4-bis(2-hydroxyethyl)amino-2-nitrophenyl]morpholine

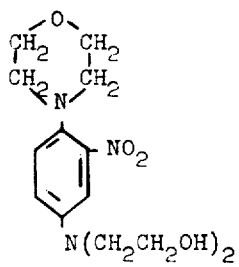

A mixture of:

| 4-fluoro-3-nitro-N,N-bis | | |
|---|---|---|
| (2-hydroxyethyl)aniline | 9.76 | g. |
| morpholine | 17.4 | g. |
| water | 150 | ml. | was maintained at reflux for 8 hours, the whole extracted with chloroform, and on evaporating on steam bath, a dark oil resulted. This was shaken with 50 ml. of warm water and the water decanted. This operation was repeated several times until all morpholine was removed. A brown oil was obtained which after drying finally solidified after standing several days.

Yield: 4.9 g. of red-brown, microcrystalline product (=40% theoretical), m.p. 66°–68°C, chromatographically pure.

EXAMPLE 21

Preparation of 1-[4-bis(2-hydroxyethyl)amino-2-nitrophenyl]piperidine

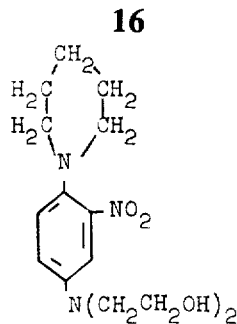

A mixture of:

| 4-fluoro-3-nitro-N,N-bis | | |
|---|---|---|
| (2-hydroxyethyl)aniline | 9.76 | g. |
| piperidine | 16.8 | g. |
| water | 150 | ml. | was maintained at reflux for 8 hours and aqueous layer decanted frm the oil. The latter was shaken with 50 ml. of warm water, and the water then decanted. This was repeated several times until all piperidine was removed. After drying and standing, the oil crystallized out.

Yield: 10.0 g. of orange-brown crystals (=81% theoretical), m.p. 82°–83°C., chromatographically pure.

EXAMPLE 22

Preparation of $N^4,N^4$-Bis(2-hydroxyethyl)-2-nitro-p-phenylenediamine

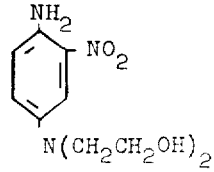

A mixture of:

| 4-fluoro-3-nitro-N,N-bis | |
|---|---|
| (2-hydroxyethyl)aniline | 97.6 g. |
| conc. aqueous ammonia | 300 g. | was heated in a stainless steel autoclave in an oil bath of 90°C. for 20 hours. The maximum pressure attained was 70 to 72 P.S.I. After cooling to 5°C., the contents consisted of a thick slurry of brown crystals. After adding 40 g. of solid NaCl, the crystals were filtered off, washed with cold water, and dried in vacuo at 60°C.

Yield: 85.8 g. of dark brown, metallic crystals, m.p. 103°–104°C., corresponding to 89% of theory. Chromatogram (paper and thin layer) shows only a trace of the starting material.

EXAMPLE 23

Preparation of Nitro-p-phenylenediamine

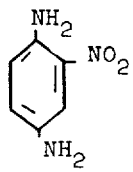

A mixture of:

| | | |
|---|---|---|
| 4-fluoro-3-nitroaniline | 23.40 | g. |
| conc. aqueous ammonia | 135 | g. | was heated in a stainless steel autoclave in an oil bath of 100°C. for 22 hours. Pressure rose to 85 P.S.I. After cooling to 5°, the thick slurry of crystals obtained was ground in a mortar. Fine needles were filtered off, washed with cold water, and dried in vacuo at 60°C.

Yield: 19.1 g. of dark brown, metalic needles, m.p. 129°–130°C, corresponding to 83% of theory. Chromatogram (paper and thin layer) shows a larger trace of starting material to be present than for the preceding example.

EXAMPLE 24

Preparation of
4-N-hydroxyethylamino-3-nitroacetanilide

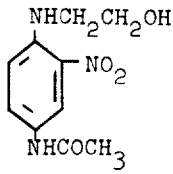

25.0 g. of 4-fluoro-3-nitroaniline was suspended in 250 ml. water and with good stirring 70 ml. of acetic anhydride dropped in. The mixture reached 45°C. and was then heated to 90°C to complete the acetylation. On cooling, to approximately 5°C, a thick slurry of crystals was formed, which were separated by filtration, washed with water to neutrality, and dried in vacuo at 60°–70°C.

Yield: 30.4 g. (=95.7% of theory) of acetylated product of m.p. 140°–142°C.

A mixture of 19.8 g of this product, 13.5 g. of monoethanolamine, 100 ml. water and 5.2 g. of $Na_2CO_3$ anhydrous was added, was heated to reflux (103°) and held here for 15 minutes. The color of the mixture rapidly changed from the original pale yellow to the final deep red orange. After cooling to about 5°C., the solid which separated was filtered off, washed with 550 ml. water to neutrality and dried in vacuo at 60°C.

Yield: 22.5 g. of deep orange, fine needles (i.e. 95% of theory), m.p. 179°–180°C.; m.p. of recrystallized (water) product was 183°–185°C.

By boiling with 10% NaOH the substance was converted to 4-N-hydroxyethylamino-3-nitroaniline.

EXAMPLE 25

Preparation of
4-N-hydroxyethylamino-3-nitro-p-toluenesulfanilide

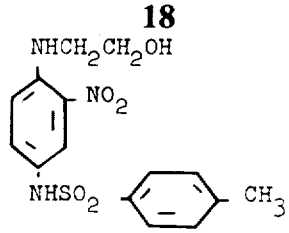

A mixture of:

| | | |
|---|---|---|
| 4-fluoro-3-nitroaniline | 15.6 | g. |
| pyridine | 30 | ml. |
| isopropanol | 70 | ml. |
| p-tosylchloride | 25 | g. | was held for 30 minutes at 76°C. Then the solution was poured on to a mixture of 125 ml water and 125 ml ice, whereby first an oily product separated, which soon solidified and was collected on filter, finely ground on mortar, washed with water to neutrality, and dried in vacuo at 60°–70°C.

Yield: 30.9 g. of pale yellow, crystalline, tosylated product, i.e. 100% of theory, m.p. 147°–148°C. A mixture of 15.42 g. of this product, 7.0 g. of monoethanolamine, 50 ml. of water and 2.7 g. of $Na_2CO_3$ (anhydrous) was added, was heated to reflux (103°C), and here held for 25 minutes. The color changed from pale yellow to brown-orange. After cooling to about 50°C., the solid which separated was filtered off, washed with 270 ml. water to neutrality, and dried to constant weight.

Yield: 8.3 g. (=57% theory) of orange powder, m.p. 159°–160°C. M.P. has not changed after recrystallization from water-isopropanol.

Although the invention has been described with reference to specific forms thereof, it will be understood that many changes and modifications may be made without departing from the spirit of this invention.

What is claimed is:

1. Compounds of formula

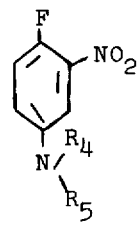

wherein $R_4$ and $R_5$ are selected from the group consisting of mono-, di-, or trihydroxyalkyl having 1 to 6 carbon atoms and alkyl having 1 to 6 carbon atoms.

2. Compounds according to claim 1 wherein $R_4$ and $R_5$ are mono-, di- or trihydroxyalkyl having 1 to 6 carbon atoms.

3. A compound according to claim 2 wherein $R_4$ and $R_5$ are $\beta$-hydroxyethyl.

* * * * *

UNITED STATES PATENT AND TRADEMARK OFFICE
CERTIFICATE OF CORRECTION

PATENT NO. : 3,944,612
DATED : March 16, 1976
INVENTOR(S) : MILOS S. BIL

It is certified that error appears in the above-identified patent and that said Letters Patent are hereby corrected as shown below:

First page, under heading "Related U.S. Application Data" change "November 2, 1970" to -- November 2, 1967 --

Signed and Sealed this

Sixth Day of February 1979

[SEAL]

Attest:

RUTH C. MASON
*Attesting Officer*

DONALD W. BANNER
*Commissioner of Patents and Trademarks*